US008887572B2

(12) United States Patent
Turner

(10) Patent No.: US 8,887,572 B2
(45) Date of Patent: *Nov. 18, 2014

(54) SYSTEM AND METHODS TO DETERMINE AND MONITOR CHANGES IN MICROSTRUCTURAL PROPERTIES

(75) Inventor: Joseph A. Turner, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 826 days.

This patent is subject to a terminal disclaimer.

(21) Appl. No.: 12/984,291

(22) Filed: Jan. 4, 2011

(65) Prior Publication Data
US 2011/0098942 A1 Apr. 28, 2011

Related U.S. Application Data

(63) Continuation of application No. 12/079,925, filed on Mar. 28, 2008, now Pat. No. 7,942,058, and a continuation-in-part of application No. 11/724,025, filed on Mar. 14, 2007, now abandoned.

(60) Provisional application No. 60/920,991, filed on Mar. 30, 2007, provisional application No. 60/782,608, filed on Mar. 15, 2006.

(51) Int. Cl.
*G01N 29/04* (2006.01)
*B61K 9/08* (2006.01)
*G01N 29/12* (2006.01)
*G01N 29/24* (2006.01)

(52) U.S. Cl.
CPC *B61K 9/08* (2013.01); *G01N 29/12* (2013.01); *G01N 29/2418* (2013.01); *G01N 2291/02881* (2013.01); *G01N 2291/102* (2013.01); *G01N 2291/2623* (2013.01)

USPC .................................. 73/602; 73/636; 73/643

(58) Field of Classification Search
USPC ..................................... 73/602, 636, 639, 643
See application file for complete search history.

(56) References Cited

U.S. PATENT DOCUMENTS 3,768,306 A * 10/1973 Stearns ........................... 73/625
3,960,005 A 6/1976 Vezina
(Continued)

FOREIGN PATENT DOCUMENTS

| EP | 2182351 A1 | 5/2010 |
|---|---|---|
| JP | 07174643 | 7/1995 |
| SU | 1801844 | 3/1993 |

OTHER PUBLICATIONS

Ghoshal, Goutam et al., "Diffuse Ultrasonic Backscatter in a Two-Dimensional Domain", ACTA Mechanica, vol. 205, No. 1-4, pp. 35-49, Apr. 21, 2009.

(Continued)

*Primary Examiner* — J M Saint Surin
(74) *Attorney, Agent, or Firm* — Davis, Brown, Koehn, Shors & Roberts, P.C.; Sean D. Solberg

(57) ABSTRACT

A system and methods with which changes in microstructure properties such as grain size, grain elongation, texture, and porosity of materials can be determined and monitored over time to assess conditions such as stress and defects. An example system includes a number of ultrasonic transducers configured to transmit ultrasonic waves towards a target region on a specimen, a voltage source configured to excite the first and second ultrasonic transducers, and a processor configured to determine one or more properties of the specimen.

20 Claims, 8 Drawing Sheets

(56) References Cited

U.S. PATENT DOCUMENTS

| | | | |
|---|---|---|---|
| 4,010,636 A | | 3/1977 | Clark et al. |
| 4,174,636 A | * | 11/1979 | Pagano ............................ 73/636 |
| 4,283,953 A | | 8/1981 | Plona |
| 4,435,984 A | | 3/1984 | Gruber |
| 4,570,487 A | * | 2/1986 | Gruber ............................ 73/624 |
| 4,961,346 A | * | 10/1990 | Salvado et al. ................. 73/644 |
| 5,020,371 A | | 6/1991 | Panetti |
| 5,335,184 A | | 8/1994 | Hildebrand |
| 5,341,683 A | | 8/1994 | Searle |
| 5,386,727 A | | 2/1995 | Searle |
| 5,390,544 A | | 2/1995 | Madras |
| 5,721,685 A | | 2/1998 | Holland et al. |
| 5,753,808 A | | 5/1998 | Johnson |
| 6,044,698 A | | 4/2000 | Bryan |
| 6,119,353 A | | 9/2000 | Gronskov |
| 6,430,875 B1 | | 8/2002 | Clark et al. |
| 6,647,891 B2 | | 11/2003 | Holmes et al. |
| 6,742,392 B2 | | 6/2004 | Gilmore et al. |
| 7,016,825 B1 | * | 3/2006 | Tryon, III ......................... 703/6 |
| 7,305,885 B2 | * | 12/2007 | Barshinger et al. ............. 73/602 |
| 7,403,296 B2 | | 7/2008 | Farritor et al. |
| 7,480,601 B2 | * | 1/2009 | Tryon, III ......................... 703/7 |
| 7,755,774 B2 | | 7/2010 | Farritor et al. |
| 7,920,984 B2 | | 4/2011 | Farritor |
| 7,937,246 B2 | | 5/2011 | Farritor et al. |
| 7,942,058 B2 | | 5/2011 | Turner |
| 8,027,820 B2 | * | 9/2011 | Tryon, III ......................... 703/7 |
| 8,393,218 B2 | * | 3/2013 | Yamano et al. ................. 73/632 |
| 2004/0003662 A1 | | 1/2004 | Kenderian et al. |
| 2005/0072236 A1 | | 4/2005 | Heyman et al. |
| 2006/0136152 A1 | | 6/2006 | Takahashi |
| 2007/0214892 A1 | | 9/2007 | Turner et al. |
| 2010/0288049 A1 | | 11/2010 | Hoyt |
| 2011/0166827 A1 | | 7/2011 | Farritor |
| 2012/0132005 A1 | | 5/2012 | Turner et al. |

OTHER PUBLICATIONS

International Search Report and Written Opinion issued in PCT/US2011/062383, mailed Mar. 5, 2012, 11 pages.

Lu, Sheng et al., "Exception Criteria in Vertical Track Deflection and Modulus", 2007 ASME/IEEE Joint Rail Conference & Internal Combustion Engine Spring Technical Conference, Mar. 13, 2007, Pueblo, CO USA, 12 pages.

Lu, S. et al. "Measurement of Vertical Track Modulus From a Moving Railcar," Proceedings of the AREMA 2006 Annual Conference, Louisville, KY, Sep. 17, 2006.

Lu, S. et al., "On the Relationship Between Load and Deflection in Railroad Track Structure," Proceedings of the AREMA 2008 Annual Conference, Salt Lake City, UT, Sep. 21, 2008.

* cited by examiner

SYSTEM AND METHODS TO DETERMINE AND MONITOR CHANGES IN MICROSTRUCTURAL PROPERTIES

CROSS-REFERENCE TO RELATED APPLICATIONS

This application is a continuation application of U.S. application Ser. No. 12/079,925, filed Mar. 28, 2008, entitled "System and Methods to Determine and Monitor Changes in Microstructural Properties," which claims priority to U.S. Provisional Application No. 60/920,991, filed Mar. 30, 2007, entitled "Detection System and Methods," and which is a continuation-in-part application of U.S. application Ser. No. 11/724,025, filed Mar. 14, 2007, entitled "Systems and Methods to Determine and Monitor Changes in Rail Conditions Over Time," which claims priority to U.S. Provisional Application No. 60/782,608, filed Mar. 15, 2006, entitled "Systems and Methods for Monitoring Longitudinal Stress in Rail," all of which are incorporated herein by reference in their entirety for all purposes.

This invention was made with government support under DRFR53-04-G00011 awarded by the Federal Railroad Administration and DE-FG02-01ER45890 awarded by the Department of Energy. The government has certain rights in the invention.

TECHNICAL FIELD

The present invention relates generally to a system and methods with which changes in microstructural properties such as grain size, grain elongation, texture, and porosity of materials can be determined and monitored over time to assess conditions such as stress and defects.

BACKGROUND

For purposes of this application, the present invention is discussed in reference to polycrystalline materials, but the present invention is applicable to any heterogeneous material such as paracrystalline materials. A polycrystalline material is a material that is made of microstructure comprising many smaller crystallites, or grains, with varying orientation. The variation in direction of the grains, known as texture, can be random or directed depending on growth and processing conditions. The grains also vary in size, deformation (elongation), and void spaces between grains, or porosity.

A polycrystalline material includes almost all common metals and many ceramics. A polycrystalline material is a structure of a solid, for example, steel or brass, that when cooled form liquid crystals from differing points within the material.

One example of a polycrystalline material is steel. For exemplary purposes, the present invention is discussed in reference to steel in the form of railroad rail, but the present invention is applicable to any material in any form or size or shape for which material properties are desired to be determined and monitored over time such as to assess conditions of stress and defects.

Rail is used on railways, otherwise known as railroads, which guide trains without the need for steering. As shown in FIG. 1, rail tracks 20 typically consist of two parallel rails 22, 23. Rails are typically made from steel, which can carry heavier loads than other materials. Rails 22, 23 are laid upon cross ties 24 that are embedded in ballast 26. Cross ties 24, also known as sleepers, ensure the proper distance, or gauge, between the rails 22, 23. Cross ties 24 also distribute the load, or force, on the rails 22, 23 over the ballast 26. Plates 28 are positioned on top of cross ties 24 to receive rails 22, 23. The rails 22, 23 are then fastened to the cross ties 24 by a fastener 30, for example, with rail spikes, lag screws, bolts, or clips. The fastener 30 is driven through the plate 28 and into the cross tie 24.

Shown in FIGS. 2 and 3 is a representative rail 22. Rail 22 consists of rail sections 22', 22". Rail sections 22', 22" can be aligned and secured together by joint bars 32 (FIG. 2) or welding 34 (FIG. 3). Most modern railways use welding to align secure rail sections, known as continuous welded rail ("CWR"), to form one continuous rail that may be several miles long. In this form of track, the rails are welded together such as by thermite reaction or flash butt welding.

Longitudinal stress is a problem over large regions of rail track. Stress is a measure of force per unit area, typically expressed in pound-force per square inch (psi). The term "longitudinal" means "along the major (or long) axis" as opposed to "latitudinal" which means "along the width", transverse, or across.

Longitudinal rail stress ("LRS") is usually related to rail contractions and expansions due to changes in temperature. Longitudinal rail stress leads to failure, which is loss of load-carrying capacity. Examples of failure include, for example, buckling and fracture. Rail experiences tensile stress in cold temperatures, which can lead to fracture or separation of a rail into two or more pieces. In hot temperatures rail experiences compression stress, which can lead to buckling or warping. Tensile stress is a stress state causing expansion (increase in volume) whereas compression stress is a stress state causing compaction (decrease in volume). It should be noted that a zero stress state is when the material does not experience any stress. Failures, among other things, cause derailments and service disruption.

The ability to measure longitudinal rail stress is a primary challenge in the railway industry. The presence of large regions of rail track reduces the ability of rail to expand and contract easily due to daily and seasonal temperature changes. Thus, high longitudinal stresses can develop, which, in turn, leads to possible failure.

In the United States, from years 2001-2003, there were over 98 derailments associated with track buckling. Damage estimates for these derailments exceed $37 million. In addition, over 900 additional incidents associated with rail stress were reported. LRS is an on-going major difficulty for railroads.

There has been extensive research to develop a non-destructive method to measure LRS. Current techniques include strain gauges (e.g., available from Salient Systems) and rail uplift (e.g., the VERSE system by Vortok, Inc.). There are downfalls to these current techniques. Strain gauges only provide measurements related to stress in a local, or confined area. Additionally, strain gauges present difficulty in determining the zero stress state. Measurement by rail uplift is costly and requires a section of rail to be detached from the ties. Techniques, such as these single-point measurements, make it difficult to obtain measurements on large regions of rail track. Besides steel, a variety of other polycrystalline materials may need to be assessed to determine and monitor microstructural properties over time.

Traditional ultrasonic inspection methods include stress induced displacement, angle of incidence, differential pulse transit, pulse count, and signal relativity. With induced displacement, an ultrasound wave is introduced into the material using a transducer at a specified angle of incidence. The signal is received by an array of sensors at a predetermined spacing a distance from the transmitter after passing through and reflected from the bottom surface of the material. The spacing between the transmitter and receiving sensors is modified by a hydraulic servo-controller to maximize the signal at the center receiving sensor. Material height is measured independently in order to quantify the travel distance of the incident wave.

Angle of incidence introduces a longitudinal wave into the top surface of the material. The refraction path through the material and reflected from the bottom surface is measured by sensors. The angle of the transmitting transducer is adjusted to maintain a constant signal at the receiving sensors. This change in angle is used to determine the stress states of the material.

Differential pulse transit uses a pair of pulse trains coupled into the material. The time difference measured in the equivalent pulses in the pair of pulse trains is then related to the stress state of the material. The baseline travel time is based on measurements on stress free material. Differences in the travel time are indications of compressive or tensile stress.

The pulse count method introduces a pulse train into the material. The pulses are spaced such that the stress states will cause them to overlap or spread in time. The number of pulses is counted to extract the stress state provided the pulse separation is appropriately chosen.

Two successive sinusoidal waves are introduced into the material with signal relativity. As the waves propagate, their spacing in time changes based upon the stress state. This spacing is determined by quantifying the amplitude of the received signal relative to the incident waves.

Problems with these methods are that they all require introduction of the ultrasonic wave through the top surface of the material and reflection of the incident waves from the bottom surface of the material without considering the microstructural properties of the material.

An improved ultrasonic inspection system and methods are needed for any and all types of materials regardless of size and shape to assess microstructure properties of the material. Determining and monitoring material properties of microstructure over time may lead to specific types of processing of these materials in order to reduce or eliminate stress or defects in the material. For example, a specific sequence of a heat treatment process, such as annealing or sintering, may be utilized to alleviate significant alterations of microstructure during processing.

There is a demand, therefore, for an improved ultrasonic inspection method that is reliable, practical, and cost effective with which changes in microstructural properties can be determined and monitored over time, including conditions related to stress and defects. The present invention satisfies that demand.

SUMMARY

The present invention determines and monitors microstructural properties of materials. In one embodiment, the present invention is an ultrasonic inspection system and methods utilizing ultrasonic wave speed. In another embodiment, the present invention is an ultrasonic inspection system and methods utilizing scatter of an ultrasonic wave. Utilizing scatter of an ultrasonic wave eliminates exploitation of the subsurface longitudinal wave which requires an angle of incidence. Scatter is a general physical process whereby propagating waves are forced to deviate from a straight trajectory because of non-uniformities in the material through which it passes.

According to the present invention, an improved ultrasonic inspection system and methods utilize scatter of an ultrasonic wave to determine and monitor changes in material properties, such as changes in microstructure grain size, grain elongation, texture, and porosity. Microstructural properties of materials can be determined and monitored over time to assess conditions such as stress and defects. The present invention determines and monitors microstructural properties of materials of any size and shape such as planar, cylindrical, and spherical.

For purposes of this application, the present invention is discussed in reference to rail tracks on railways, but the present invention is applicable to any structure, including geological structures. For example, the present invention can determine and monitor changes in conditions of buildings, bridges, fault lines for predicting earthquakes, and land mass for prospecting oil.

In one embodiment, the present invention is directed to a system and methods with which changes in microstructure properties can be determined and monitored over time using scatter of an ultrasonic wave. A transducer holder is positioned on a specimen. For purposes of this application, the term "specimen" is any heterogeneous material for which conditions such as stress or defects are desired to be determined and monitored. A transducer holder includes a top surface and a bottom surface in which a plurality of guides are created. The plurality of guides extends from the top surface to the bottom surface of the transducer holder. Each guide is angularly positioned within the transducer holder with respect to the top surface. A transducer is positioned within each guide and a voltage source excites an ultrasonic wave to propagate through the specimen. The voltage source may include, for example, a signal generator device or a laser. A laser generates heat creating an ultrasonic sound wave, whereas one type of signal generator device generates electromagnetic waves coupled into ultrasonic waves. In embodiments that use a laser to generate a signal, the laser is fired at the material, thereby generating heat and an ultrasonic wave which may be received by a laser interferometer. As a result, the ultrasonic wave is scattered within the specimen. Each transducer receives a signal from the scattered ultrasonic wave and a digital signal processor digitizes the signals. A pulse-echo technique is appropriate when using the same transducer to send and receive an ultrasonic wave for embodiments exploiting scatter of an ultrasonic wave.

In a specific embodiment, rail conditions can be determined and monitored over time using scatter from an ultrasonic wave. In the broadest form, the present invention includes a transducer holder, a voltage source, an energy conversion device, an electronic test device, a database, a computing device, and a navigation device.

A voltage source, such as a signal generator device, excites a pulse from a transducer that is ultimately useful to non-destructively assess material conditions in rail. One embodiment of a signal generator device is a pulser-receiver. A pulser-receiver includes a pulser that generates pulses, such as electrical signals, and thereby ultrasonic sound waves, and a receiver to receive them.

The signal generator device introduces a signal into the rail. The angle at which the signal is introduced for rail steel is between a range of 0 degrees and 33 degrees. An energy conversion device converts signals from one form to another. One such type of energy conversion device is a transducer, which includes such types as electromagnetic, electrochemical, electromechanical, electroacoustic, photoelectric, electrostatic, or thermoelectric. Transducers typically communicate from a transmitting transducer to a receiving transducer.

One embodiment of the invention includes a system and methods wherein the energy conversion device is securable to the rail track of a railway. Another embodiment of the invention includes a system and methods wherein the energy conversion device is securable to a coupling device, such as an applicator. The applicator is any homogeneous material that allows the energy conversion device to introduce the signal at a specific angle to propagate into the rail.

Another embodiment of the invention includes a system and methods in which the energy conversion device is securable to the wheels of a railway car to implement a "rolling" system. A "rolling" system allows the present invention to become mobile, thereby allowing rail conditions to be determined and monitored over large regions of rail track. In this embodiment, a fluid-filled roller is used. The rollers can further house the energy conversion device, such as a transducer. The energy conversion device is positioned within the roller such that it introduces the signal into the rail at the desired angle. It is further contemplated that a "rolling" system can be integrated with other rail measurement techniques, or with defect detection vehicles such as those used by Sperry Rail Service or Herzog Services, for example.

An electronic test device captures data, such as voltage, current, ultrasonic wave information, temperature, date, time, position, or any measurement just to name a few. Such equipment may include an infrared temperature detector, Global Positioning System ("GPS"), voltmeter, ohmmeter, ammeter, power supply, signal generator, pulse generator, oscilloscope, and frequency counter, for example. Ultrasonic wave information can include scatter, speed, amplitude, and wavelength.

A computer system is used to calculate and store data. The computer system may be remote from, or integrated with, the ultrasonic inspection system. The computer system allows for real-time data analysis. A computer system is a machine for manipulating data according to a list of instructions. For example, a computer can be a laptop computer, handheld device, or personal digital assistant.

With embodiments using scatter of an ultrasonic wave, a computer processor calculates a spatial variance value from the measured signals received by the transducer. A computer database analyzes the value by comparing the calculated spatial variance to a theoretical spatial variance value to assess changes in microstructure properties. The theoretical spatial variance value is stored in the database as a first set of data. The database may further store the calculated spatial variance values as a second set of data. It is contemplated that the first set of data or second set of data is historical data taken over time at the same location on the specimen. Various calculations can be performed on the first set of data and second set of data, such as an average of one set of data or a comparison between both sets of data.

With embodiments using speed of an ultrasonic wave, a computer processor uses an autocorrelation component to calculate the wave speed from the measured signals received by the transducer.

The present invention also includes a database for the storage of a grouping of data. A grouping of data can include one or more sets of data. One or more sets of data can be compared with other one or more sets of data, as well as utilized for various calculations. For example, a first set of data can be compared with a second set of data. Likewise, data can be computed and analyzed, for example, to determine the stress state or defects in a specimen. The database can be retained on a computer used to conduct much of the analyses or retained on a separate computer or computing device, or even an on-board or integrated computer system.

Data includes, for example, location measurement such as from a Global Positioning System ("GPS"), wave speed, temperature, and the grain size, grain elongation, texture, and porosity of materials. It is further contemplated that baseline data can be established for comparison with the grouping of data. The baseline data can be, for example, "stress-free" or "zero" measurements. If baseline data is not established, one grouping of data can be compared to another grouping of data. The database may also include acoustoelastic constants, which are properties of a material that correlate changes in wave speed to changes in stress or defects.

In one example, the improved system and methods of the present invention permit changes in rail conditions, most specifically longitudinal rail stress, to be assessed and monitored over time dynamically and nondestructively. One embodiment of the system includes a signal generator device that generates a signal that is transmitted to an energy conversion device. The energy conversion device converts the signal to a sound wave that propagates through the rail and is returned to the energy conversion device. The navigation device determines position of the sound wave at specific time intervals. A navigation device is a device with position or location capability, such as a Global Positioning System ("GPS"). An electronic test device captures this data and stores the data to a database.

In embodiments using scatter, the computing device processes the data pertaining to microstructural properties such as grain size, grain elongation, texture and porosity, which govern the scatter of the ultrasonic wave. The ultrasonic wave is associated with longitudinal and shear wave scattering manifested through spatial variance.

In embodiments using wave speed, the computing device processes the data pertaining to position of the sound wave at specific time intervals to compute wave speed. The computer system analyzes waves, such as longitudinal, shear and Lamb waves. The wave speed at specific intervals of time as a function of position is also stored in the database for comparison to previous or subsequent data to determine and monitor changes in rail conditions.

According to the present invention, increasing wave speeds indicates an increase in longitudinal rail stress potentially leading to rail breaks while decreasing wave speeds indicates a decrease in longitudinal rail stress potentially leading to rail buckling.

The present invention has an objective of providing a system and methods to determine and monitor changes in microstructural properties such as grain size, grain elongation, texture, and porosity of materials to assess conditions such as stress and defects.

The present invention has another objective of providing a system and methods to determine and monitor changes in material microstructure such as rail conditions, including conditions related to stress and defects.

Another object of the present invention is to exploit ultrasonic waves at high frequencies, such as frequencies greater than 10 Megahertz, although any frequency is contemplated.

Another object of the present invention is to measure rail stress over large regions of rail track to mitigate stress-related issues, such as fractures and buckling.

The present invention increases rail track safety by predicting failures before they occur.

Another object of the present invention is to provide a system and methods for rail track maintenance.

While current technology is focused on single-position measurements, the present invention provides multiple position measurements of stress in rail.

Another object of the present invention is to provide a database for mass storage of data. The database can be accessed for analysis of the data including various calculations to determine and monitor changes in rail conditions over time.

Another object of the present invention is to utilize a navigation system to accurately determine position of the failure.

These and other advantages, as well as the invention itself, will become apparent in the details of construction and operation as more fully described and claimed below. Moreover, it should be appreciated that several aspects of the invention can be used in other applications where monitoring of stress would be desirable.

DETAILED DESCRIPTION

The present invention will now be described in detail with reference to certain embodiments thereof as illustrated in the accompanying drawings. In the following description, numerous specific details are set forth in order to provide a thorough understanding of the present invention and how it may be applied. It will be apparent, however, to one skilled in the art, that the present invention may be practiced without some or all of these specific details. In other instances, well-known process steps and/or structures have not been described in detail to prevent unnecessarily obscuring the present invention.

Figure 1:
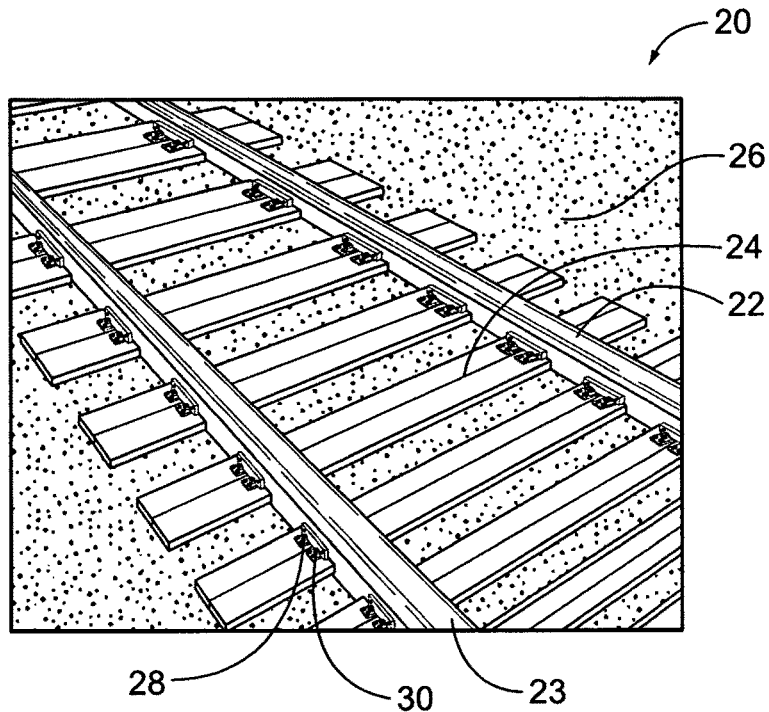
FIG. 1 illustrates rail tracks.
Figure 2:
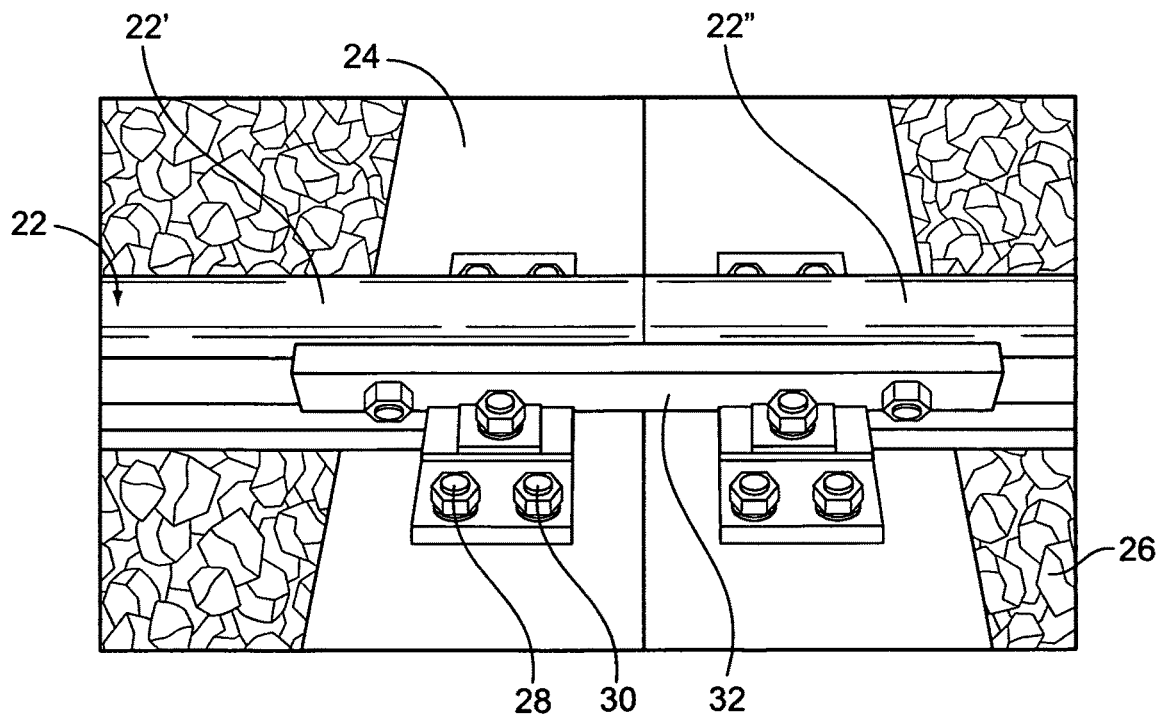
FIG. 2 illustrates rail tracks aligned and secured together by joint bars.
Figure 3:
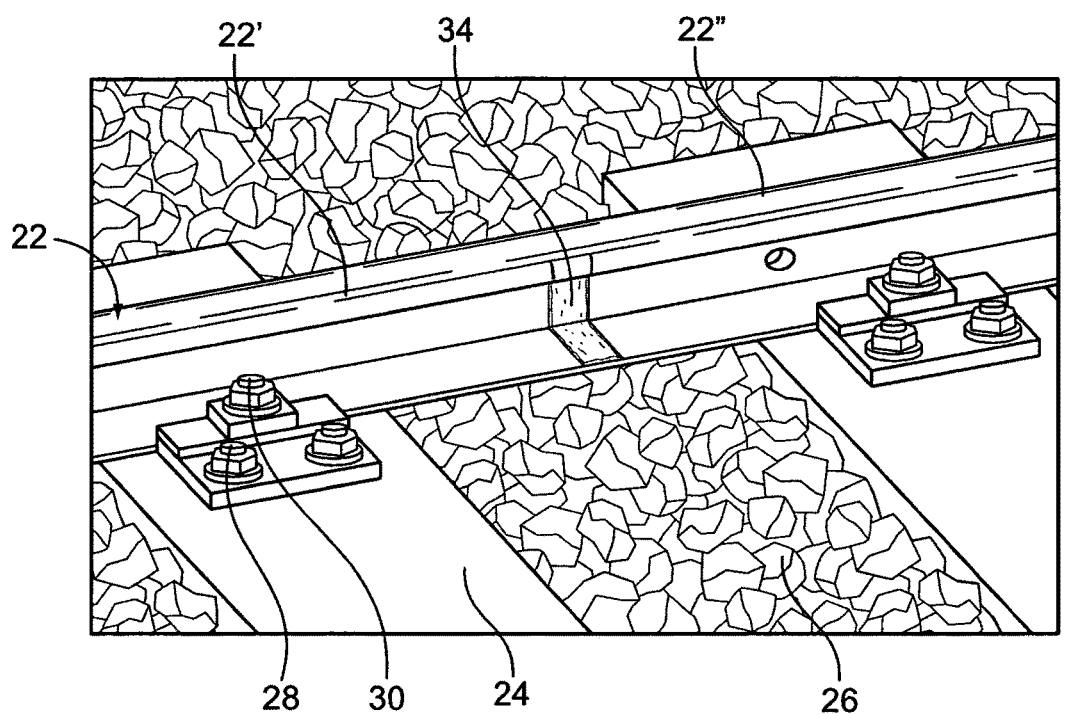
FIG. 3 illustrates rail tracks aligned and secured together by welding.
Figure 4:
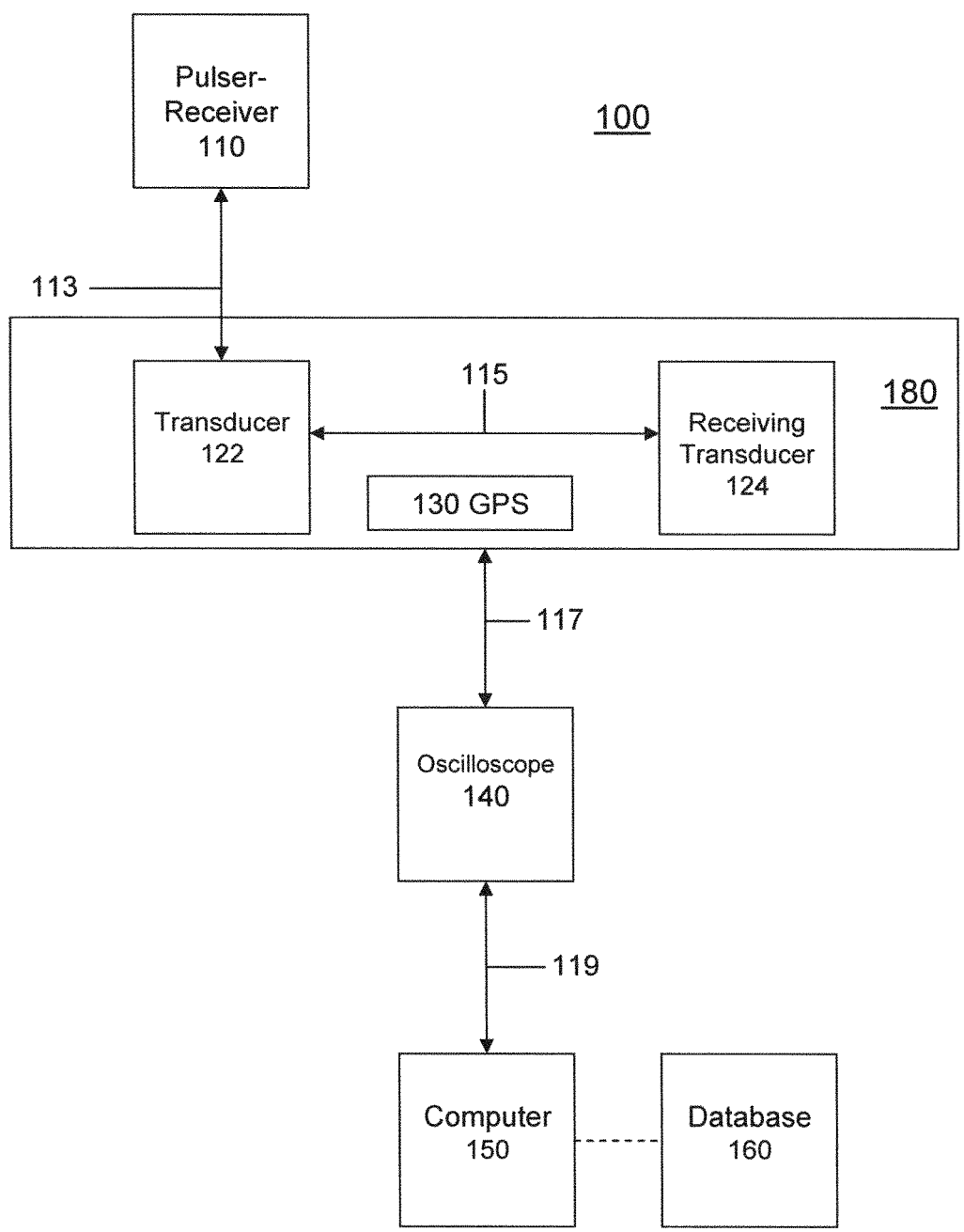
FIG. 4 is a block diagram for determining and monitoring microstructural properties utilizing ultrasonic wave speed according to the present invention.

An embodiment utilizing ultrasonic wave speed of the system and methods of the present invention are illustrated as a block diagram 100 in FIG. 4. In this embodiment, a pulser-receiver 110 generates an electrical signal that is transmitted 113 to a transducer 122. The transducer 122 converts the electrical signal to an ultrasonic wave 115 that propagates through the rail 180 to a receiving transducer 124. The GPS 130 determines position of the sound wave 115 at specific time intervals. An oscilloscope 140 captures measurements of data transmitted 117, such as ultrasonic wave information, temperature, date, time, and position, and provides the data via transmission 119 to the computer 150 for processing. The computer 150 can further include a database 160 for storage of the data.

In another embodiment, a laser is used to generate a signal by firing the laser at a rail, thereby generating heat and an ultrasonic wave which may be picked up by a receiving transducer 124.

The computer 150 may include an autocorrelation component for embodiments of the present invention that utilize wave speed to correlate changes in wave speed to changes in stress or defects. An autocorrelation component assists in calculating the travel time of the ultrasonic wave. The travel time is then used to calculate the ultrasonic wave speed. If the initial electrical signal generated from the transducer 122 includes a set of voltages $V_i$ at times $t_i$, then the autocorrelation formula is defined as:

$$r_k = \frac{\sum_{i=1}^{N-k}(V_i - \overline{V})(V_{i+k} - \overline{V})}{\sum_{i=1}^{N}(V_i - \overline{V})^2}, \text{ where } \overline{V} = \frac{1}{N}\sum_{i=1}^{N}V_i.$$

Figure 10:
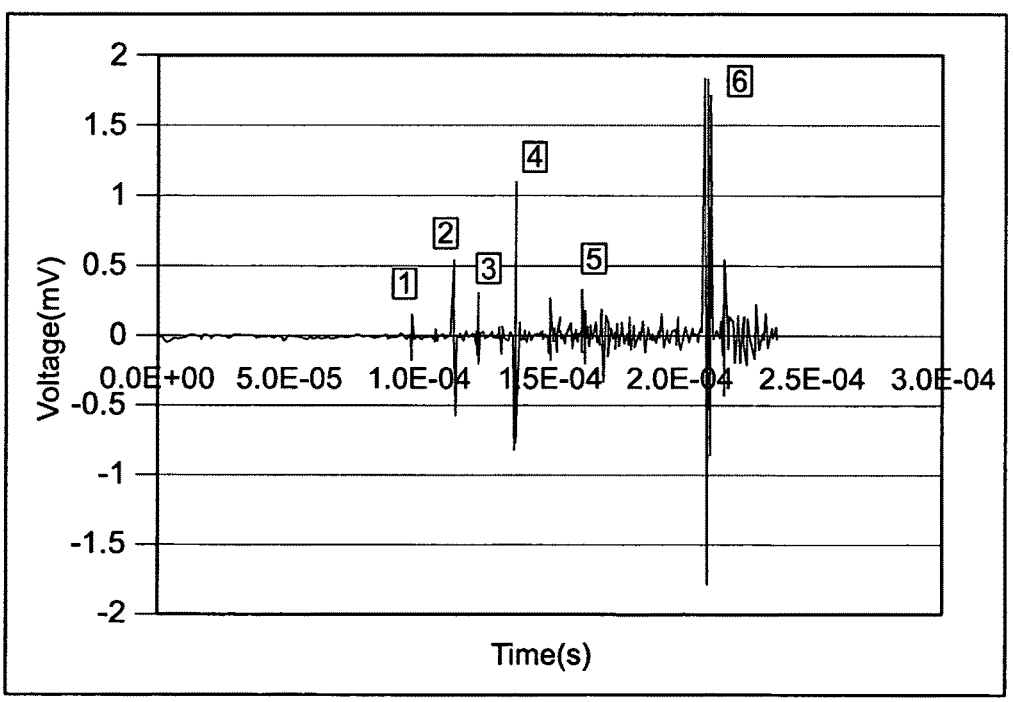
FIG. 10 illustrates the measurements taken from the system of FIG. 9.

Maxima in the vector r determines the travel times, otherwise referred to herein as the speed, of the ultrasonic wave. The travel times are dictated by the peak(s) of the ultrasonic wave (see FIG. 10). This data is stored in the database 160 and used for comparison with other measurements (baseline, past or subsequent).

The computer utilizes the autocorrelation formula to calculate the wave speed of the ultrasonic sound wave. The wave speed is calculated by dividing transducer separation distance by the travel time of the sound wave. This wave speed data, along with other data such as temperature, date, time, and position of the sound wave at specific intervals determined by the navigation device, are stored onto a database 160.

Figure 5:
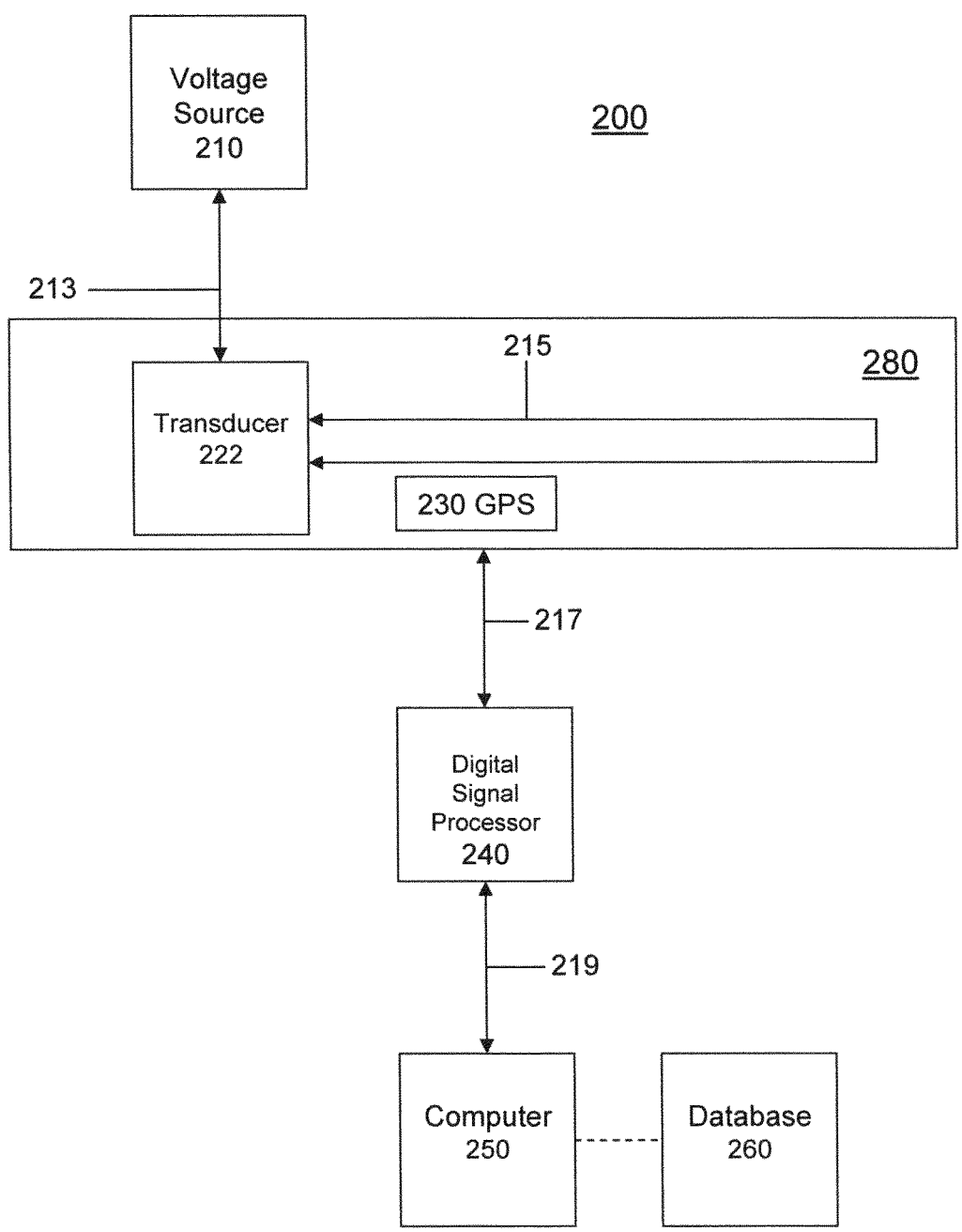
FIG. 5 is a block diagram for determining and monitoring microstructural properties utilizing scatter of an ultrasonic wave according to the present invention.

FIG. 5 is a block diagram 200 for determining and monitoring microstructural properties utilizing scatter of an ultrasonic wave according to the present invention. In this embodiment, a voltage source 210 generates an electrical signal that is transmitted 213 to excite transducer 222. The transducer 222 converts the electrical signal to an ultrasonic wave 215 that propagates through the specimen 280. The ultrasonic wave 215 is also received by transducer 222 utilizing a pulse-echo technique. It is further contemplated that a GPS 230 may determine position of the ultrasonic wave 215 at specific time intervals. A digital signal processor 240, for example, an oscilloscope, captures transmitted 217 data from the ultrasonic wave such as grain size, grain elongation, texture, and porosity. Temperature may be measured independently using, for example, an infrared temperature detector. The digital signal processor 240 provides the data via transmission 219 to the computer 250 for processing. Numerous signals are used to calculate a spatial variance value. The spatial variance is calculated to determine changes in the microstructure.

The spatial variance of the signals is calculated by first determining the spatial average:

$$b(t) = \frac{1}{M}\sum_{i}^{M}V_i(t)$$

where M is the number of positions and $V_i(t)$ is the measured signal at position i. The spatial variance is defined as:

$$n(t) = \sqrt{\frac{1}{M}\sum_{i}^{M}(V_i(t) - b(t))^2}$$

and is determined on a computer or other signal processing board. This spatial variance represents a measure of the microstructure state in the specimen. Changes in the microstructure are determined by examining how the theoretical spatial variance differs from the measured value used to determine the stress state in the sample.

The computer 250 can further include a database 260 for storage of the data.

The data stored within the database 260 includes grain size, grain elongation, texture, and porosity at specific intervals of time as a function of position. Data also includes grain size, grain elongation, texture, and porosity which can be determined from changes in wave speed. This data is compared to a grouping of data stored within the database 260 to determine and monitor changes in the condition of the specimen 280.

Figure 6:
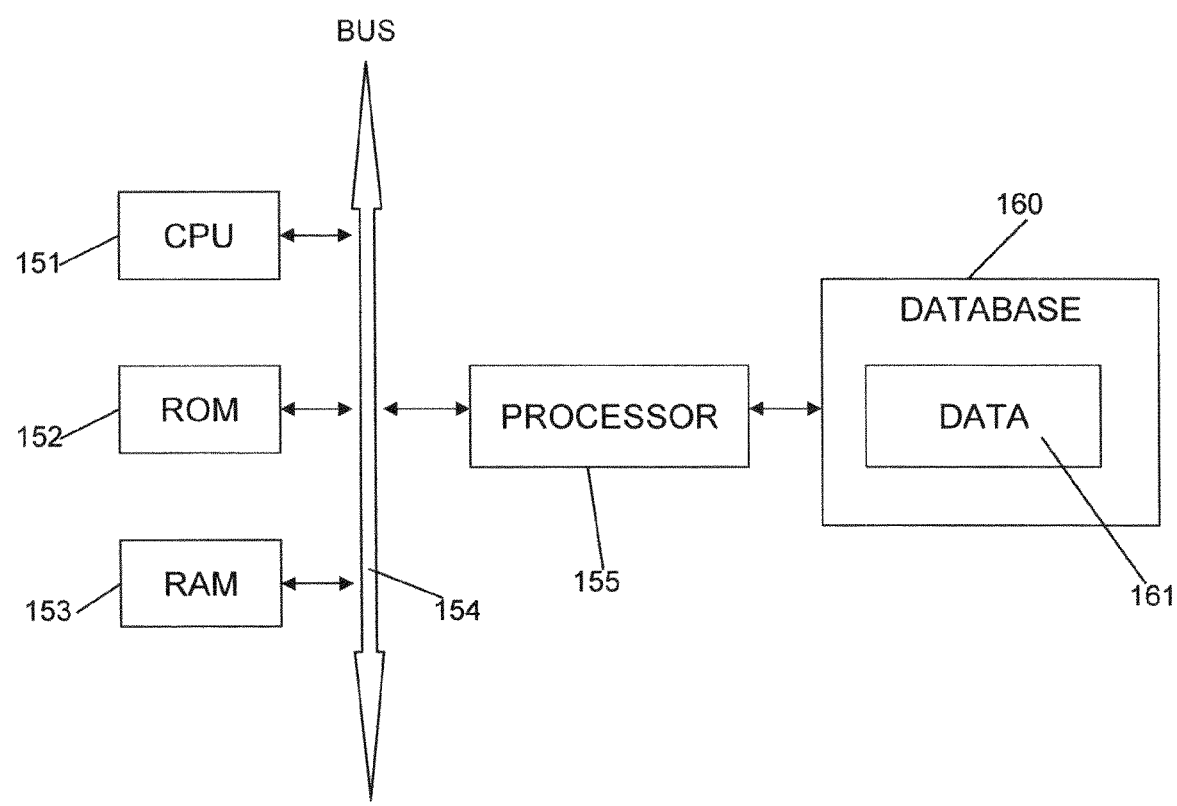
FIG. 6 is a block diagram of a general computer system according to the present invention.

FIG. 6 is a block diagram showing the structure of a general computer system 150 according to the present invention. The system 150 includes a central processing unit (CPU) 151, a read-only memory (ROM) 152, a random access memory (RAM) 153, a processor 155, and a database 160, all interconnected by a system bus 154. The database 160 serves as a storage device and may further include data 161.

Figure 7:
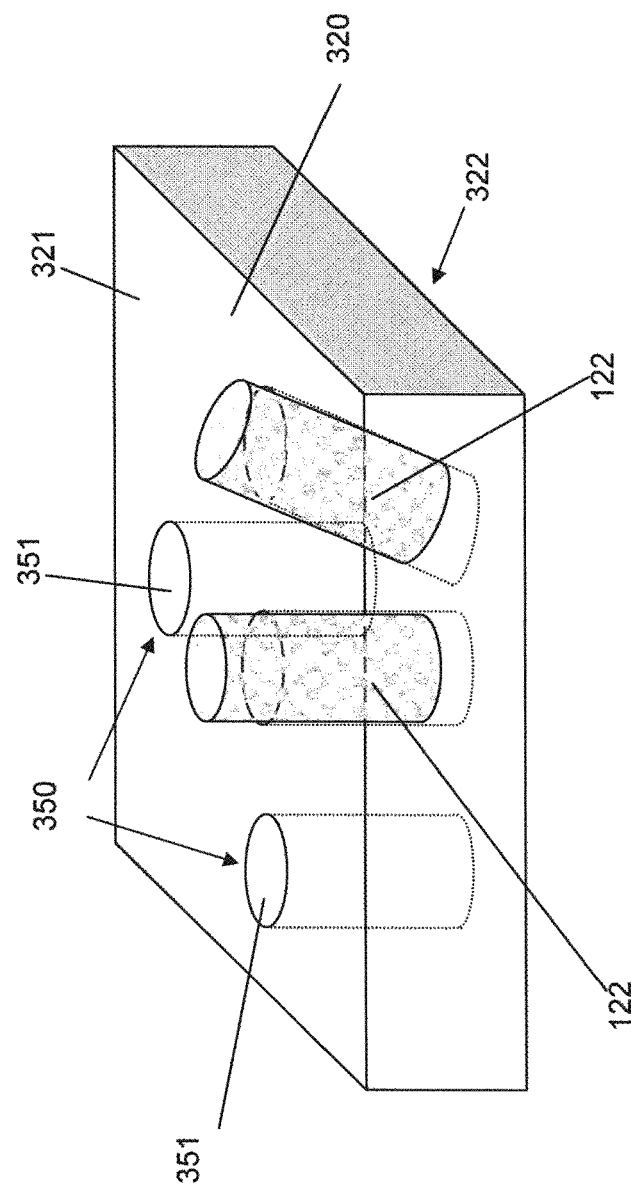
FIG. 7 illustrates an embodiment of the present invention, a transducer holder for use with a planar specimen.

FIG. 7 illustrates an embodiment of the present invention, transducer holder 320, for use with a planar specimen of a polycrystalline material. This embodiment is designed for measurements on planar or flat specimens such as plates, beams, and rails to name a few. The transducer holder 320 is made from any homogeneous material, such as plexiglass, and includes a top surface 321 and a bottom surface 322. The transducer holder 320 has at least two guides 350, wherein the guide extends through the top surface 321 and bottom surface 322 of the transducer holder 320. The guides 350 are oriented at specific angles between and including zero to thirty degrees with respect to the top surface 321. As shown in FIG. 7, the guides 350 are cylindrical through-holes 351, although any sized or shaped guides are contemplated.

The guides 350 act as channels for placement of the transducers 122 (or 222). A voltage source (not shown) excites the transducers 122 (or 222) to propagate ultrasonic waves. Ultrasonic waves travel through a coupling medium, such as air, water, glycerine, or any viscous fluid in the specimen. Each transducer 122 (or 222) then receives a signal after the wave returns. The signal is then digitized and placed in a pulse-echo technique. A pulse-echo technique is appropriate when using the same transducer 122 (or 222) to send and receive an ultrasonic wave. Numerous signals are used to calculate on a spatial average value. Spatial averaging is calculated to determine changes in the microstructure of a specimen. It is desirable to collect the numerous signals by moving the transducer holder 320 to various positions on the specimen. Typically each position is at least 0.5 mm away from the other positions and at least 20 positions are needed to have a relatively smooth result.

Figure 8:
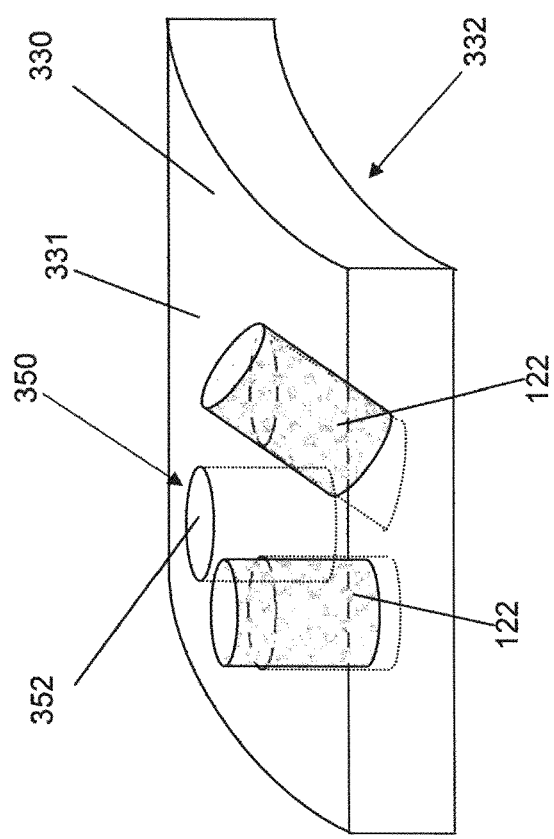
FIG. 8 illustrates an embodiment of the present invention, a transducer holder for use with a cylindrical specimen.

FIG. 8 illustrates an embodiment of the present invention, transducer holder 330, for use with a cylindrical specimen of a polycrystalline material. This embodiment is designed for measurements on cylindrical, or curved, specimens such as packaging or a pressure vessel. The transducer holder 330 is made from any homogeneous material, such as plexiglass, and includes a top surface 331 and a bottom surface 332. Again, transducer holder 330 is placed on the specimen for which microstructure properties are desired. The transducer holder 330 has at least two guides 350, wherein the guide extends through the top surface 331 and bottom surface 332 of the transducer holder 330. The guides 350 are oriented at specific angles between and including zero to thirty degrees with respect to the top surface 321. As shown in FIG. 8, the guides 350 are cylindrical through-holes 352 although any sized or shaped guides are contemplated.

Transducers 122 (or 222) are placed within the guides 350 and a voltage source (not shown) excites the transducers 122 (or 222) to propagate ultrasonic waves. Each transducer 122 (or 222) then receives a signal after the wave returns, which is then digitized.

Figure 9:
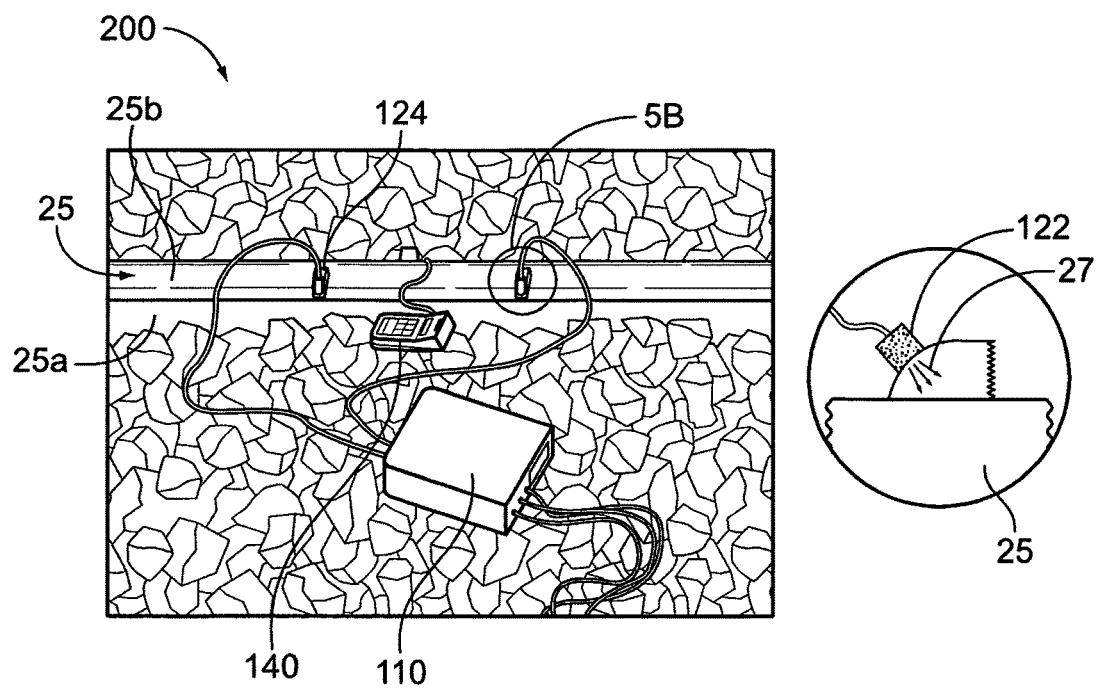
FIG. 9 illustrates a system for determining and monitoring stress in rail according to the present invention.

FIG. 9 illustrates an embodiment of a system 500 for determining and monitoring stress in rails according to the present invention. A transducer 122 and receiving transducer 124 are sized and shaped such that each may be positioned on a surface of the rail 25 such as a side surface 25A, or top surface 25B of a rail 25 through a coupling device 27, such as applicator. In embodiments that use scatter of an ultrasonic wave, the transducer 122 receives the ultrasound wave scatter without the need for transducer 124.

The coupling device 27 may be in the form of a wedge or other shape to permit easy adherence to the rail surface 25A, 25B. The coupling device 27 is preferably formed of a material to facilitate the transmission of the ultrasonic wave by the transducer 122 and the receptor of the ultrasonic wave by the receiving transducer 124. Acrylic is one of the many materials that may be used for this purpose. Other embodiments of the system and methods utilize the positioning of the transducers 122, 124 on the wheels of a railway car.

With reference to FIG. 9, embodiments that use scatter of an ultrasonic wave include a voltage source 110 that sends a voltage signal to the transducer 122. The transducer 122 converts the voltage signal to an ultrasonic sound wave that propagates through the rail 25 and is received by transducer 124. The transducer 122 amplifies and digitizes the sound wave into signals. The signals received from the transducer 122 may be acquired such as with an oscilloscope 140 and conveyed to a database, for example, within a laptop or equivalent computer (not shown). The database is used for data analysis of the signals. The computer utilizes an auto-correlation formula to calculate the travel time of the sound wave. The wave speed is then calculated by dividing transducer separation distance by the travel time of the sound wave.

This wave speed data, along with other data such as temperature, date, time, and position of the sound wave at specific intervals determined by the navigation device, are stored in a database. Again, in embodiments that use ultrasonic wave scatter, the computer calculates a spatial variance value. This spatial variance data, along with other data such as grain size, grain elongation, texture, and porosity, are stored into the database. Data such as temperature can be taken by the transducers 122, 124 on the rail 25. Likewise, the navigation device (not shown) can take the position data at the location where the temperature data is taken.

The database 160 may store the data at specific intervals of time as a function of position. The database 160 can be on the computer 150 or on a separate computer.

The computer 150 compares data of the database 160. A first set of data can be compared to other sets of data. The first set of data can be one data point, a plurality of data points, a base line or control data points. A second set of data points can be one data point or a plurality of data points for comparison with the first set of data points. The comparison between data points determines abnormalities or changes, if any, between the data over time. The database would store theoretical spatial variance values as well as historical values measured at the same location for comparison.

According to the present invention, a first set of data points, such as spatial variance, is compared to a second set of data points. A comparison resulting in an increase in wave speeds indicates an increase in longitudinal rail stress potentially leading to rail breaks while a comparison resulting in a decrease in wave speeds indicates a decrease in longitudinal rail stress potentially leading to rail buckling.

While endeavoring in the foregoing specification to draw attention to those features of the invention believed to be of particular importance it should be understood that the Applicants claim protection in respect of any patentable feature or combination of features hereinbefore referred to and/or shown in the drawings whether or not particular emphasis has been placed thereon. While the apparatus and method herein disclosed forms a preferred embodiment of this invention, this invention is not limited to that specific apparatus and method, and changes can be made therein without departing from the scope of this invention, which is defined in the appended claims.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A system for analyzing stress in a polycrystalline specimen, comprising:
    a. a first ultrasonic transducer configured to transmit a first ultrasonic wave at a first angle of incidence towards a target location on a specimen;
    b. a second ultrasonic transducer configured to transmit a second ultrasonic wave at a second angle of incidence towards the target location on the specimen;
    c. a voltage source configured to excite the first and second ultrasonic transducers, wherein each transducer is configured to operate in pulse-echo mode to receive a scattered ultrasonic signal from the specimen in response to the first and second ultrasonic waves;
    d. a processor configured to calculate a statistical spatial variance value from the plurality of scattered ultrasonic signals as a function of spatial position, wherein the scattered ultrasonic signal received by the first and second transducers comprises both longitudinal and shear waves; and
    e. database of theoretical spatial variance values wherein said statistical spatial variance values for the longitudinal and shear waves are compared to the theoretical variance values to assess changes in microstructure properties of the specimen over time.

2. The system of claim 1, wherein the microstructural properties assessed include grain size, grain elongation, texture, and porosity at specific intervals of time as a function of position.

3. The system of claim 2, wherein the microstructural properties are determined as a function of wavespeed.

4. The system of claim 3, wherein the spatial variance of the signals is calculated by first determining the spatial average.

5. The system of claim 4, wherein the processor further comprises an autocorrelation component configured to utilize wave speed to correlate changes in wave speed to changes in stress or defects.

6. The system of claim 5, further comprising a transducer holder comprising a plurality of guides coupled to the transducer holder, each guide configured to receive a corresponding ultrasonic transducer.

7. The system of claim 6, wherein the specimen is a rail, and wherein the transducer holder is configured to move along the rail.

8. The system of claim 7, wherein the transducer holder comprises a fluid-filled roller.

9. The system of claim 6, wherein the transducer holder is cylindrically shaped.

10. The system of claim 1, further comprising a navigation device configured to determine position information of the first and second ultrasonic waves at specific time intervals.

11. A system for analyzing stress in the grains of a rail, comprising:
    a. a first ultrasonic transducer configured to transmit a first ultrasonic wave at a first angle of incidence towards a target location on a rail;
    b. a second ultrasonic transducer configured to transmit a second ultrasonic wave at a second angle of incidence towards the target location on the rail;
    c. excitation means for pulsing the first and second transducers, wherein each transducer operates in pulse-echo mode and is configured to receive a scattered ultrasonic backscatter signal from the rail in response to the first and second ultrasonic waves;
    d. processing means for calculating a statistical spatial variance value from the scattered ultrasonic signals as a function of spatial position and comparing the spatial variance value to one or more theoretical spatial values over time: and
    e. determining stress by assessing microstructural properties of the grains of the rail at specific intervals of time as a function of position.

12. A device for analyzing a polycrystalline specimen, comprising:
    a. a means for exciting a plurality of ultrasonic transducers to operate in pulse-echo mode to transmit multiple ultrasonic waves to a target location on a specimen;
    b. a means for digitizing scattered ultrasonic signals received from the specimen in response to the ultrasonic waves;
    c. a means for calculating a statistical spatial variance value from the ultrasonic backscatter signals as a function of spatial position; and
    d. a means for comparing the spatial variance value to a theoretical spatial variance value stored in a database to assess a change in one or more properties of the grains of the polycrystalline specimen.

13. The system of claim 11, wherein the microstructural properties assessed include grain size, grain elongation, texture, and porosity at specific intervals of time as a tinction of position.

14. The system of claim 13 wherein the microstructural properties are determined as a function of wavespeed.

15. The system of claim 14, wherein the spatial variance of the signals is calculated by first determining the spatial average.

16. The system of claim 15, wherein the processing means further comprises an autocorrelation component configured to utilize wave speed to correlate changes in wave speed to changes in stress or defects.

17. The system of claim 13, further comprising a transducer holder comprising a plurality of guides coupled to the transducer holder, each guide configured to receive a corresponding ultrasonic transducer.

18. The system of claim 17, wherein the transducer holder is configured to move along the rail.

19. The system of claim 17, wherein the transducer holder comprises a fluid-filled roller.

20. The system of claim 17, wherein the transducer holder is cylindrically shaped.

* * * * *